United States Patent [19]
Flanagan

[11] Patent Number: 6,131,586
[45] Date of Patent: Oct. 17, 2000

[54] ACTIVE DENTAL FLOSS CONTAINER

[76] Inventor: Lloyd D. Flanagan, 103 Prince Edward, Pointe Claire, Quebec, Canada, H9R 4C6

[21] Appl. No.: 09/329,115

[22] Filed: Jun. 9, 1999

[30] Foreign Application Priority Data

Jun. 12, 1998 [CA] Canada ................................. 2237024

[51] Int. Cl.[7] .................................................. A61C 15/00
[52] U.S. Cl. ........................................... 132/325; 132/323
[58] Field of Search .................................... 132/321, 323, 132/324, 325

[56] References Cited

U.S. PATENT DOCUMENTS

| | | | |
|---|---|---|---|
| 4,050,470 | 9/1977 | Miller | 132/323 |
| 4,920,993 | 5/1990 | Mackie | 132/324 |
| 4,926,820 | 5/1990 | Wearn | 132/323 |
| 5,199,452 | 4/1993 | Cheng | 132/323 |
| 5,503,168 | 4/1996 | Wang | 132/323 |
| 5,678,579 | 10/1997 | Meyer et al. | 132/324 |
| 5,680,875 | 10/1997 | Winters | 132/323 |
| 5,692,532 | 12/1997 | Gabrovsek | 132/323 |

*Primary Examiner*—Todd E. Manahan
*Attorney, Agent, or Firm*—Eric Fincham

[57] ABSTRACT

A dental floss container and dispenser having first and second sections, the first section being designed to hold a floss spool and having floss guide means to guide the floss from the floss spool to exteriorly thereof, the first section also selectively permitting and preventing the dispensing of floss from the floss spool, and the second section being designed to cut the floss and grip the floss. Preferably, both sections are ergonomically configured and sized to fit within a user's hand with each section having an ergonomic design to accept the last three fingers of the user's hand to thereby encourage use of a user's index fingers to guide the floss.

10 Claims, 4 Drawing Sheets

ACTIVE DENTAL FLOSS CONTAINER

BACKGROUND OF THE INVENTION

The use of dental floss is widely practiced and encouraged by dentists. Combined with brushing after meals, the use of dental floss in oral hygiene promotes healthy teeth and in particular, good oral health.

Dentists and other health professionals continue to encourage the use of flossing on a regular basis as an integral part of oral hygiene. However, there still is a certain resistance to flossing on the part of a certain portion of the public and furthermore, the technique of flossing employed by many people is not necessarily efficient in accomplishing the desired tasks. Normally, flossing is a manual operation wherein a piece of dental floss is cut from a spool of the same and is then wrapped around one or more fingers of each hand to leave a piece of active floss between the fingers. The tensioned floss is then rubbed along the sides of each tooth near the gum line to help remove plaque and food particles.

Many people find the above technique leads to discomfort as the floss is tightly wrapped around the fingers. Indeed, a certain number of users need to stop the flossing to permit blood flow to return to the fingers. This pain tends to discourage people from flossing.

The problem of dental floss waste also exists and while a certain amount of floss must be cut from the floss spool, the portion wrapped around the fingers is generally wasted.

It has been proposed in the art to provide various types of dispensers for use in flossing. However, none of these have received any wide degree of acceptance. Exemplary of such types of tools is that shown in U.S. Pat. No. 5,570,710 to Wei et al.

SUMMARY OF THE INVENTION

It is an object of the present invention to provide a floss container and dispenser system wherein floss may be drawn out from a container to a desired length and the container functions to hold one end of the floss.

It is a further object of the present invention to provide a floss container and dispenser system which provides two separate ergonomically shaped interconnecting containers which allow the floss to be spooled out between them and locked in place.

According to one aspect of the present invention, there is provided a floss container and dispenser comprising a first section and a second section, the first section having means for holding a floss spool, floss guide means to guide the floss from the floss spool to exteriorly of the first section, means to selectively permit and prevent dispensing of floss from the floss spool, and the second section having means for gripping and retaining floss dispensed from the first section.

Using the floss container and dispenser outlined above, the first and second sections may be connected together with mating male and female connectors. The first and second sections are preferably ergonomically configured to encourage the holding of the same in the palm of the hands with gripping by the last three fingers thereby leaving the index fingers to guide the floss.

BRIEF DESCRIPTION OF THE DRAWINGS

Having thus generally described the invention, reference will be made to the accompanying drawings illustrating an embodiment thereof, in which.

DESCRIPTION OF THE PREFERRED EMBODIMENTS

Figure 1:
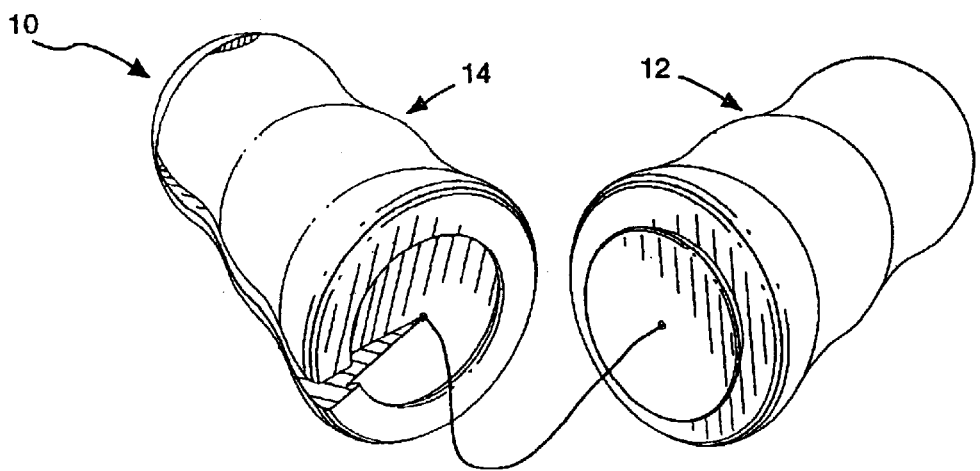
FIG. 1 is a perspective view of a dental floss container and dispenser according to the present invention.
Figure 2:
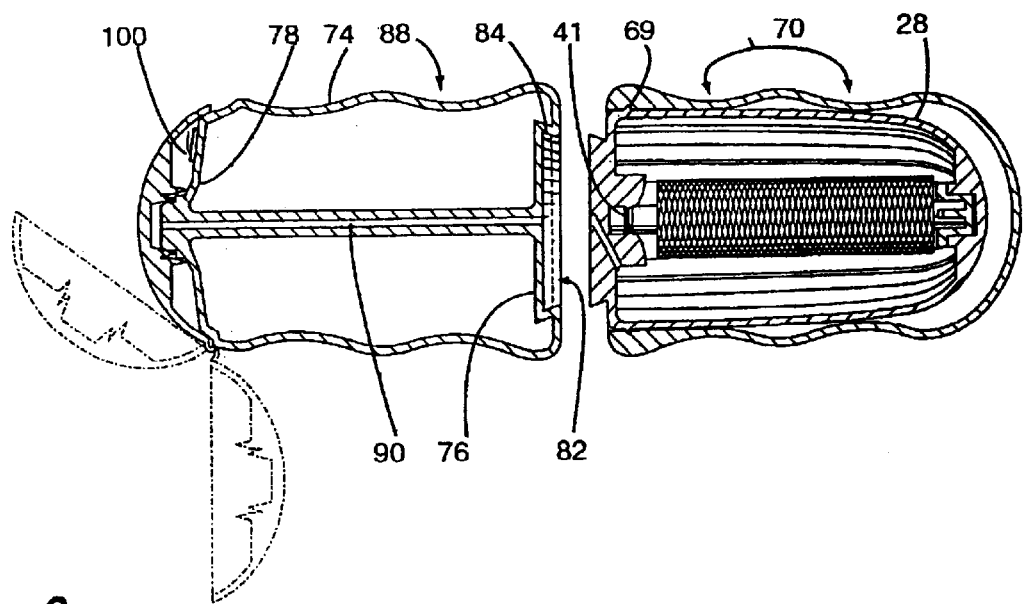
FIG. 2 is a side sectional view of the floss container and dispenser of FIG. 1.
Figure 3:
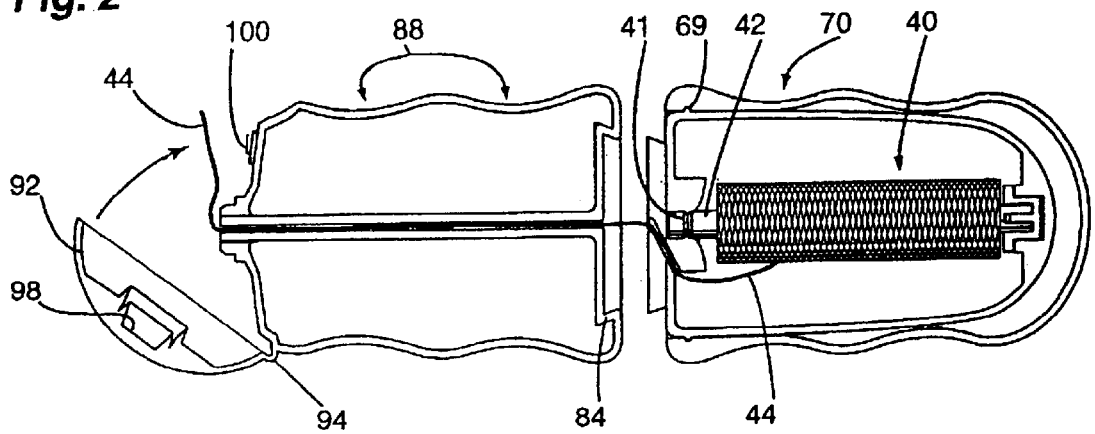
FIG. 3 is a view similar to FIG. 2 illustrating movement of the cover portion and associated cutter and the drawing being without shading for greater clarity.
Figure 4:
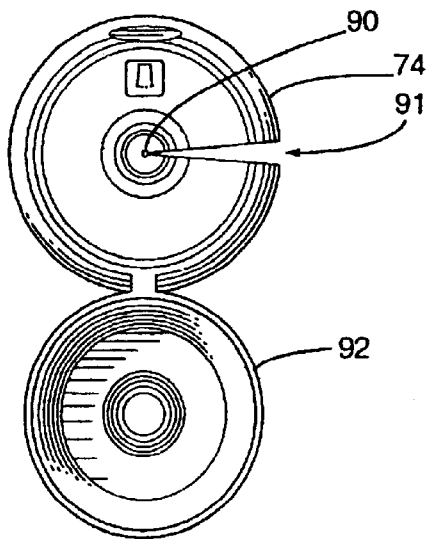
FIG. 4 is an end view as seen from the left hand side of FIG. 2 with the cover in an open position.
Figure 5:
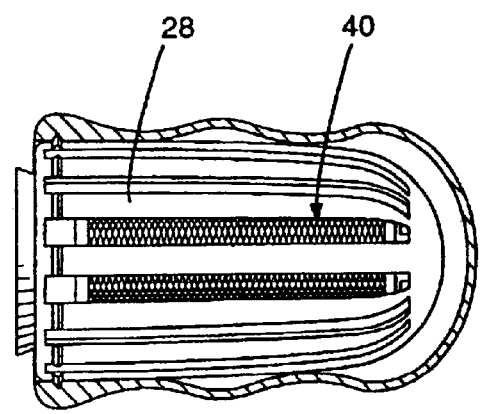
FIG. 5 is a side sectional view of an inner spool holder.
Figure 6:
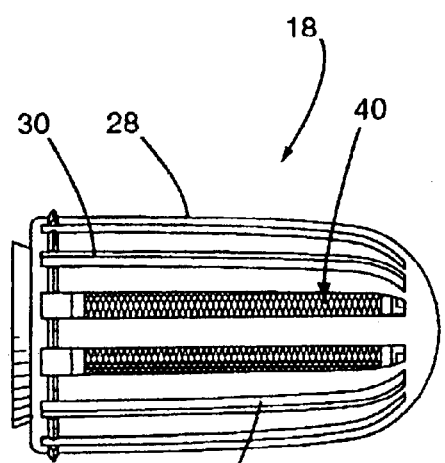
FIGS. 6 and 6A illustrate the insertion of the inner spool holder into an outer cage member.
Figure 6A:
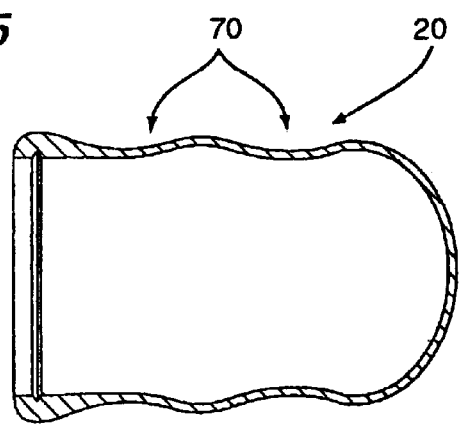

Referring to the drawings in greater detail and by reference characters thereto, there is illustrated in FIG. 1 a floss container and dispensing device generally designated by reference numeral 10.

Floss container and dispensing device 10 has a first section 12 and a second section 14 which are independent of each other and, when in an operative position, are joined only by the floss itself as will be discussed in greater detail hereinbelow.

First section 12, as may be best seen in FIGS. 2, 3, 6 and 6A, comprises an inner spool holder generally designated by reference numeral 18 and an outer cage 20. Inner spool holder 18 has a first end generally designated by reference numeral 24, a second opposed end generally designated by reference numeral 26, and a side wall 28 extending therebetween. Formed in side wall 28 are a plurality of longitudinally extending slots 30.

Figure 7:
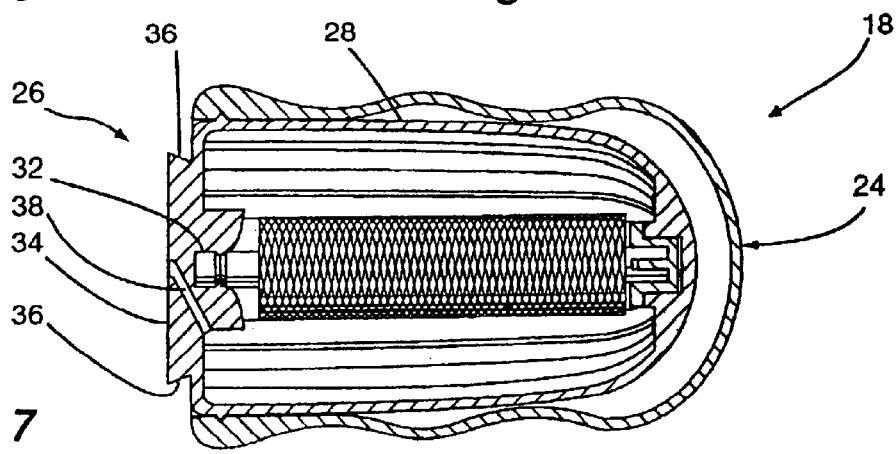
FIG. 7 is a side sectional view of the inner spool holder.

Located at first end 24 is a recess 32 formed interiorly thereof. The exteriorly facing end wall 34, as may be seen in FIG. 7, has an undercut side wall 36 for reasons which will become apparent hereinbelow. A floss guide means comprising a channel 38 is provided in end wall 34.

Mounted interiorly of inner spool holder 18 is a floss spool generally designated by reference numeral 40. Floss spool 40 comprises a core 42 having floss 44 wrapped thereabout in a conventional manner. A groove 41 is provided at one end of core 42 for releasably retaining the floss spool by engagement with a protrusion at recess 32.

Figure 10:
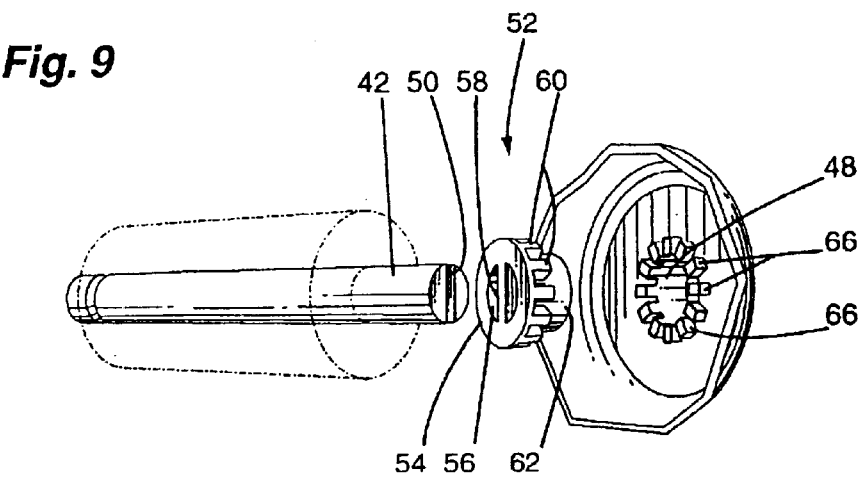
FIG. 10 is an exploded view of the floss and associated cog wheel and tooth arrangement to permit dispensing of the floss.

Second end 26 of spool holder 18 also has a recess 48 formed therein. As may be best seen in FIG. 10, core 42 has a slot formed in one end thereof. A cog wheel 52 has a top wall 54 with a recess 56 formed therein and a diametrically extending member 58 being designed to fit within slot 50 in core 42. Extending downwardly from top wall 54 are a plurality of teeth 60 and with cog wheel 52 terminating in a shaft 62.

Formed on the interior surface of second end 26 are a plurality of teeth 66 which surround recess 48. As may be seen, the arrangement is such that shaft 62 will fit within recess 48 and teeth 60 on cog wheel 52 engage teeth 66. Teeth 60 and 66 may be formed so as to be somewhat tapered to provide for a smoother meshing between the teeth.

Outer cover 20 is designed to extend about first end 24 and side wall 28 of inner spool holder 18 and be retained thereon by means of an annular protrusion 69 on side wall 28. A plurality of concave finger gripping portions generally designated by reference numeral 70 are provided on the exterior surface thereof.

Second section 14 is comprised of a first end wall generally designated by reference numeral 76 and a second end wall 78 having a side wall 74 extending therebetween.

At first end 76, there is provided a recess which is defined by an undercut side wall 84. The arrangement is such that first end 24 of first section 12 will fit within recess 82 such that the two sections may be held together.

Side wall 74 also is provided with a plurality of concave finger gripping portions 88. Formed interiorly of second section 14 is an interior channel 90 to receive the floss by means of slot 91 formed in side wall 74.

At second end 78, second section 14 is provided with a cover 92 connected by a hinge 94 to the main body portion.

As may be seen, the two sections 12 and 14 can be connected to form a compact unit for storage.

Figure 8:
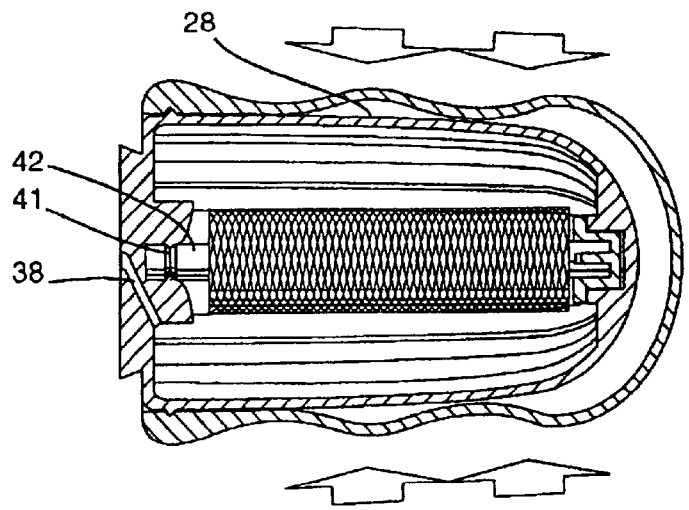
FIG. 8 is a side sectional view of the inner spool holder and outer cage with the dispenser being in a non dispensing position.
Figure 9:
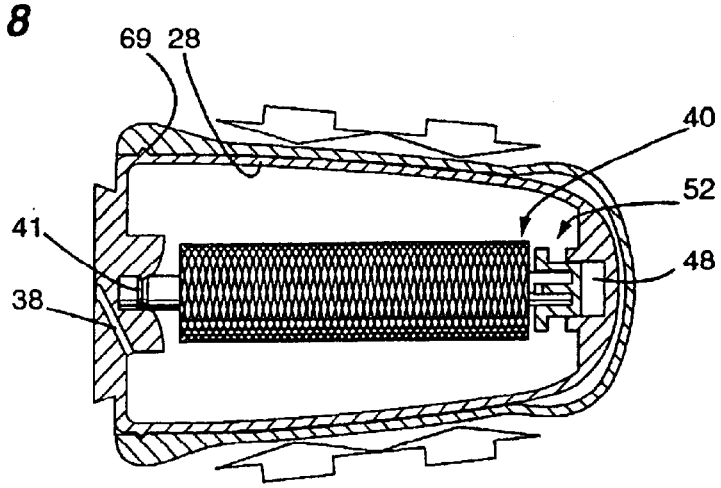
FIG. 9 is a view similar to FIG. 1 illustrating the inner spool holder and outer cage positioned to permit the dispensing of the floss.

In operation, and as may be best seen in FIGS. 8 and 9, floss spool 40 is normally maintained in a locked position by means of the interengagement of teeth 60 on cog wheel 52 and teeth 66 at second end 26. However, a squeezing action on side wall 28 will cause the disengagement of teeth 60 and 66 to thereby permit rotation of floss spool 40 and the withdrawal of floss 44 through floss guide channel 38.

After the required amount of floss is withdrawn, release of pressure on side wall 28 will again cause the interengagement of teeth 60 and 66.

Figure 11:
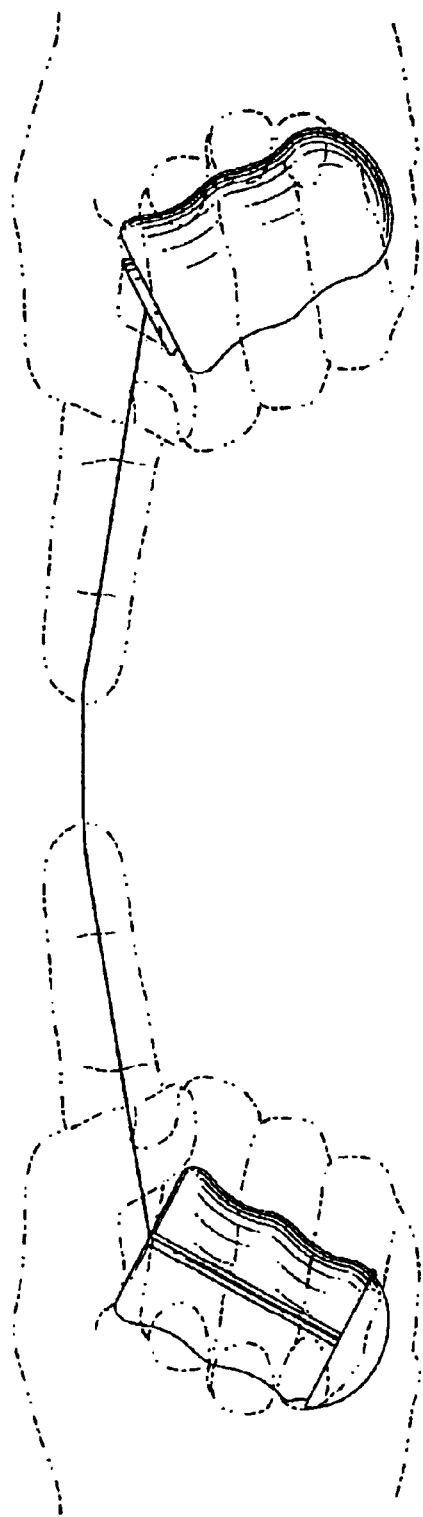
FIG. 11 is a perspective view illustrating use of the device.

The free end of the floss withdrawn from floss spool 44 is then fed into interior channel 90. Once cover 92 is closed in position, the floss is securely held in place and the length of floss between first section 12 and second section 14 may then be utilized. As may be seen in FIG. 11, the finger gripping portions 70 of sections 12 and 14 are designed to be gripped by the last three fingers leaving the index fingers free to act as a guide for the floss.

After use, the used segment of floss may be removed and cut by means of cutting means 100.

The system is easily used and is particularly useful for those with reduced manual dexterity such as those who suffer from arthritis or the elderly. The amount of floss needed during each session is reduced by one half to as much as two thirds of the usual recommendation that 18 inches of floss is needed each time.

To install a new floss spool 40, side wall 28 may be flexed and the old floss spool removed through slots 30 and a new floss spool inserted.

It will be understood that the above described embodiments are for purposes of illustration only and that changes and modifications may be made thereto without departing from the spirit and scope of the invention.

I claim:

1. A floss container and dispenser comprising:
   a first section;
   a second section;
   said first section having means for holding a floss spool comprising a flexible and resilient cage extending about said floss spool;
   floss guide means to guide floss from said floss spool to exteriorly of said first section;
   means to selectively permit and prevent dispensing of floss from said floss spool comprising a spool holder having a core to receive floss thereabout, said first section having means to receive said spool core, and means to selectively permit and prevent rotation of said spool core; and
   said second section having means for gripping and retaining floss dispensed from said first section.

2. The floss container and dispenser of claim 1 wherein both said first and second sections are ergonomically configured and sized to each fit within a user's hand, each section having means to accept the last three fingers of said user's hand to thereby encourage use of a user's index fingers to guide the floss.

3. The floss container and dispenser of claim 1 further including means for releasably connecting said first and second sections together.

4. The floss container and dispenser of claim 1 further including cutting means located on said second section.

5. The floss container and dispenser of claim 1 wherein said flexible and resilient cage has slots therein to permit the insertion of said floss spool.

6. The floss container and dispenser of claim 1 wherein said second section has a hinged cover thereon.

7. The floss container and dispenser of claim 6 wherein said second section has a centrally located channel to receive said floss.

8. The floss container and dispenser of claim 1 wherein said second section includes a centrally located interior channel to receive said floss, said channel being accessible by means of a slot formed in a side wall of said second section.

9. A floss container and dispenser comprising:
   a first section;
   a second section;
   said first section having means for holding a floss spool;
   floss guide means to guide floss from said floss spool to exteriorly of said first section;
   means to selectively permit and prevent dispensing of floss from said floss spool;
   said second section having means for gripping and retaining floss dispensed from said first section; and
   connecting means for releasably connecting said first and second sections together, said connecting means comprising a male-female coupling, said male-female coupling having apertures to permit floss to pass therethrough such that floss is completely enclosed when said first and second sections are coupled together.

10. A floss container and dispenser comprising:
   a first section;
   a second section;
   said first section having means for holding a floss spool;
   floss guide means to guide floss from said floss spool to exteriorly of said first section;
   means to selectively permit and prevent dispensing of floss from said floss spool;
   said second section having means for gripping and retaining floss dispensed from said first section comprising a centrally located interior channel to receive floss, and a slot formed in a side wall of said second section to permit threading of floss therethrough to said centrally located interior channel; and
   a hinged cover member located at an exit of said centrally located interior channel, said cover member retaining said floss when in a closed position.

* * * * *